United States Patent
Geigenmuller et al.

(10) Patent No.: US 10,525,020 B2
(45) Date of Patent: Jan. 7, 2020

(54) METABOLIC MARKERS OF ATTENTION DEFICIT HYPERACTIVITY DISORDER

(71) Applicant: Laboratory Corporation of America Holdings, Burlington, NC (US)

(72) Inventors: Ute Geigenmuller, Lexington, MA (US); Doris Damian, Lexington, MA (US); Maciej Pacula, Lexington, MA (US); Mark A. DePristo, Lexington, MA (US)

(73) Assignee: Laboratory Corporation of America Holdings, Burlington, NC (US)

( * ) Notice: Subject to any disclaimer, the term of this patent is extended or adjusted under 35 U.S.C. 154(b) by 154 days.

(21) Appl. No.: 15/019,258

(22) Filed: Feb. 9, 2016

(65) Prior Publication Data

US 2016/0231311 A1    Aug. 11, 2016

Related U.S. Application Data

(60) Provisional application No. 62/115,101, filed on Feb. 11, 2015.

(51) Int. Cl.

| | |
|---|---|
| *A61K 9/00* | (2006.01) |
| *A61K 8/02* | (2006.01) |
| *A61K 31/23* | (2006.01) |
| *A61K 31/66* | (2006.01) |
| *A61K 31/05* | (2006.01) |
| *A61Q 19/00* | (2006.01) |
| *A61K 8/24* | (2006.01) |
| *A61K 9/16* | (2006.01) |
| *A61K 8/368* | (2006.01) |
| *A61K 31/216* | (2006.01) |
| *A61K 31/60* | (2006.01) |
| *A61K 9/14* | (2006.01) |
| *A61K 47/02* | (2006.01) |
| *A61K 31/165* | (2006.01) |
| *A61K 31/4458* | (2006.01) |
| *A61K 31/138* | (2006.01) |
| *A61K 31/137* | (2006.01) |
| *A61K 31/4168* | (2006.01) |
| *A61K 31/55* | (2006.01) |
| *G01N 33/53* | (2006.01) |

(52) U.S. Cl.
CPC .......... *A61K 31/165* (2013.01); *A61K 31/137* (2013.01); *A61K 31/138* (2013.01); *A61K 31/4168* (2013.01); *A61K 31/4458* (2013.01); *A61K 31/55* (2013.01); *G01N 33/5308* (2013.01); *G01N 2800/305* (2013.01); *G01N 2800/52* (2013.01)

(58) Field of Classification Search
CPC .................................................. A61K 31/137
USPC ........................................................ 514/317
See application file for complete search history.

(56) References Cited

U.S. PATENT DOCUMENTS

| | | |
|---|---|---|
| 9,176,113 B1 | 11/2015 | Geigenmuller et al. |
| 2002/0019407 A1 | 2/2002 | Rusche et al. |
| 2007/0255113 A1 | 11/2007 | Grimes |
| 2008/0133141 A1 | 6/2008 | Frost |
| 2010/0104621 A1* | 4/2010 | Waldo .................. A61K 9/1652 424/449 |
| 2014/0065132 A1 | 3/2014 | Hsiao et al. |
| 2015/0293072 A1 | 10/2015 | Geigenmuller et al. |
| 2015/0294081 A1 | 10/2015 | Geigenmuller et al. |

FOREIGN PATENT DOCUMENTS

| | | |
|---|---|---|
| WO | WO-2004/059293 A2 | 7/2004 |
| WO | WO-2006/090185 A1 | 8/2006 |
| WO | WO-2006/121952 A2 | 11/2006 |
| WO | WO-2008/021515 A2 | 2/2008 |
| WO | WO-2015/0157601 A1 | 10/2015 |

OTHER PUBLICATIONS

S. Dolina et al., Medical Hypotheses 82 (2014) 111-116.*
Morio et al. Metabolomics reveals differential metabolic adjustments of normal and overweight subjects during overfeeding, 2015, Metabolomics, vol. 11, pp. 920-938. (Year: 2015).*
Laroche et al., The determination of indoxyl in the blood, 1933, Diagnostica tec. Lab., vol. 4, pp. 136-139, Abstract Only. (Year: 1933).*
Zgoda-Pols et al. Metabolomics analysis reveals elevation of 3-indoxyl sulfate in plasma and brain during chemically-induced acute kidney injury in mice: investigation of nicotinic acid receptor agonists, 2011, Toxicology and Applied Pharmacology, VOII. 255, pp. 48-56. (Year: 2011).*
Armstrong, M. et al., Analysis of 25 Underivatized Amino Acids in Human Plasma Using Ion-Pairing Reversed-Phase Liquid Chromatography/Time-Of-Flight Mass Spectrometry; Rapid Communications in Mass Spectrometry, 21:2717-2726, (2007).
Bourcier, S.et al., Use of Diagnostic Neutral Losses for Structural Information on Unknown Aromatic Metabolites: An Experimental and Theoretical Study, Rapid Commun Mass Spectrom. 23:(1):93-103 (2009).

(Continued)

*Primary Examiner* — Yong L Chu
(74) *Attorney, Agent, or Firm* — Kilpatrick Townsend & Stockton LLP

(57) ABSTRACT

Disclosed herein are methods for treating subjects having ADHD identifiable by levels of 3-IS in blood.

12 Claims, 1 Drawing Sheet

(56) References Cited

OTHER PUBLICATIONS

De Bree, P. K. et al., Diagnosis of Inherited Adenylosuccinase Deficiency by Thin-Layer Chromatography of Urinary Imidazoles and by Automated Cation Exchange Column Chromatography of Purines, Clin. Chim. Acta, 156(3):279-87, (1986).

Duranton, F. et al., Normal and Pathologic Concentrations of Uremic Toxins, J. Am. Soc. Nephrol. 23:1258-1270 (2012).

Evans, A. M. et al., Integrated, Nontargeted Ultrahigh Performance Liquid Chromatography/Electrospray Ionization Tandem Mass Spectrometry Platform for the Identification and Relative Quantification of the Small-Molecule Complement of Biological Systems, Anal. Chem., 81(16):6656-6667 (2009).

Jauniaux, E. et al., Free amino acids in human fetal liver and fluids at 12-17 weeks of gestation, Human Reproduction, 14:6:1638-1641, (1999).

Jiang, Q. et al., y-Tocopherol, the major form of vitamin E in the US diet, deserves more attention, American Journal of Clinical Nutrition 74, 714-722 (2001).

Jones, R. M. and Lord, C., Diagnosing autism in neurobiological research studies, Behavioural Brain Research, 251:113-124 (2013).

Kale, A. et al., Elevated amniotic fluid amino acid levels in fetuses with gastroschisis, Brazilian Journal of Medical and Biological Research, 39:1021-1025, (2006).

Lord, R. S. et al., Clinical Applications of Urinary Organic Acids, Part 2, Dysbiosis Markers, Alternative Medicine Review, 13:4:292-306, (2008).

Mochel, F. et al., Elevated CSF N-acetylaspartylglutamate in Patients with Free Sialic Acid Storage Diseases, Neurology, 74(4):302-305, (2010).

Quinones, M and Kaddurah-Daouk, R., Metabolomics Tools for identifying biomarkers for neuropsychiatric diseases, Neurobiology of Disease, 35(2):165-176, (2009).

Tanaka. K. and Hine, D. G., Compilation of Gas Chromatographic Retention Indices of 163 Metabolically Important Organic Acids, and Their Use in Detection of Patients with Organic Acidurias, J. Chromatogr., 239:301-322 (1982).

Umino, D. et al., Serum indoxyl sulfate as an early marker for detecting chronic cyclosporine nephrotoxicity, Pediatrics International 52:257-261 (2010).

Ventola, P. et al., Differentiating Between Autism Spectrum Disorders and Other Developmental Disabilities in Children Who Failed a Screening Instrument for ASD, Journal of Autism and Developmental Disorders 37:425-436 (2007).

Young, S. N. et al., Tryptophan, 5-hydroxyindoleacetic acid and indoleacetic acid in human cerebrospinal fluid: interrelationships and the influence of age, sex, epilepsy and anticonvulsant drugs, Journal of Neurology, Neurosurgery, and Psychiatry, 43:438-445, (1980).

Zheng, Z. et al., The Footprints of Gut Microbial—Mammalian Co-Metabolism, American Chemical Society, J. Proteome Res., 10:5512-5522, (2011).

Zweig, M. H. & Campbell, G., Receiver-Operating Characteristic (ROC) Plots: A Fundamental Evaluation Tool in Clinical Medicine, Clinical Chemistry 39:561-577 (1993).

* cited by examiner

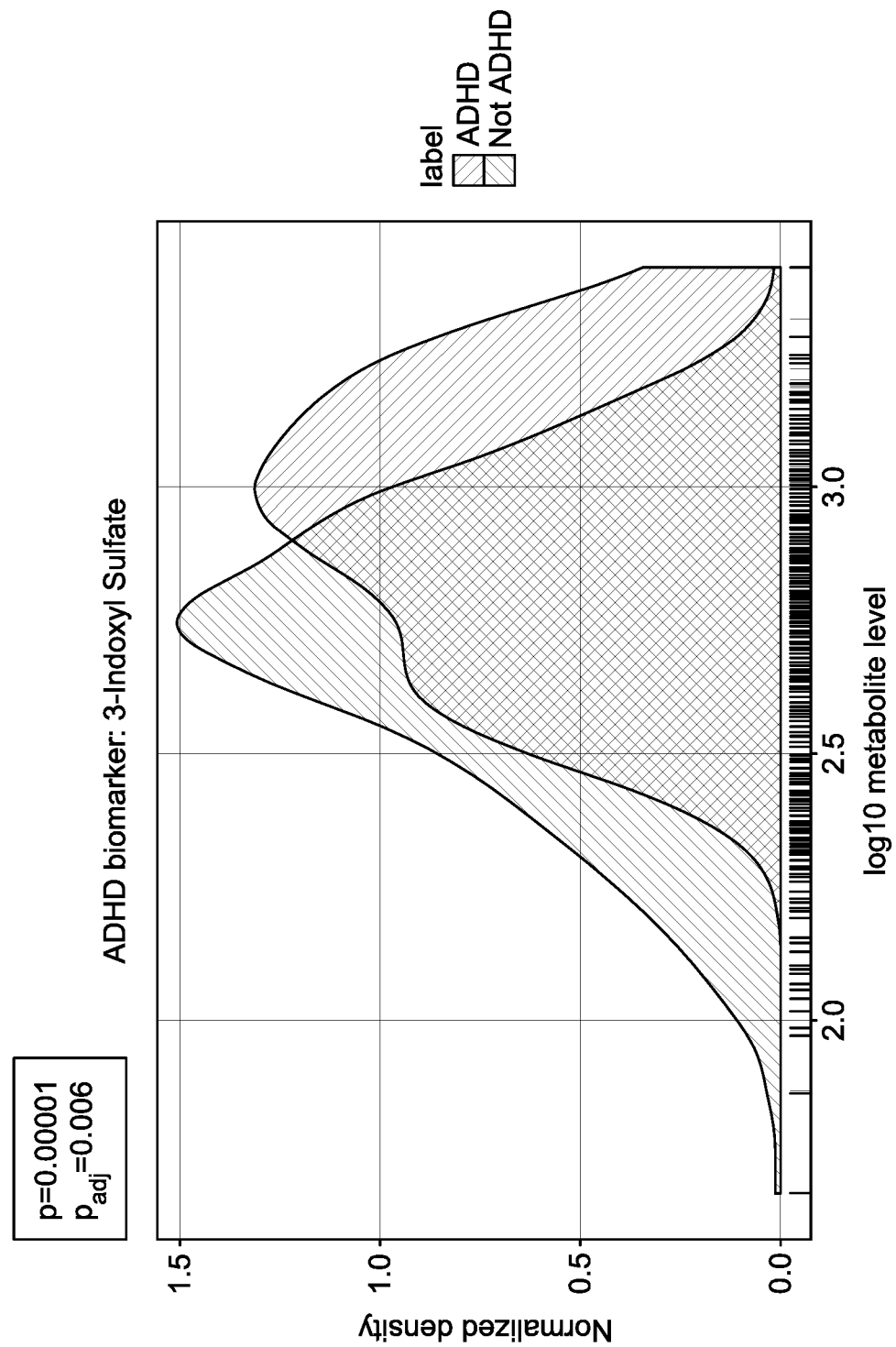

METABOLIC MARKERS OF ATTENTION DEFICIT HYPERACTIVITY DISORDER

CROSS REFERENCE TO RELATED APPLICATIONS

This patent application claims the benefit of U.S. Provisional Patent Application No. 62/115,101, filed Feb. 11, 2015, the entirety of which is incorporated herein by reference.

FIELD OF THE INVENTION

This invention relates generally to metabolic markers of Attention Deficit Hyperactivity Disorder (ADHD) individuals.

BACKGROUND

Attention Deficit Hyperactivity Disorder (ADHD) is a disorder characterized by inattention and/or difficulty staying focused as well as hyperactivity and/or difficulty in control of one's behavior. ADHD typically presents early in life (i.e. during childhood). Presently, diagnosis is typically based upon a combination of self, family and/or teacher/caretaker reports of behaviors combined with observations and input from physicians and other licensed health-care practitioners.

SUMMARY

In some embodiments, the invention provides methods for distinguishing between or among at least two conditions for diagnosis and/or risk assessment of an individual suspected of having or observed as having atypical development, wherein the at least two conditions comprise attention deficit hyperactivity disorder (ADHD) and non-attention deficit hyperactivity disorder (non-ADHD), the method comprising the steps of:

measuring a level of 3-Indoxyl Sulfate (3-IS) in a biological sample obtained from the individual;

optionally identifying, by a processor of a computing device, a difference (e.g., an absolute difference or a relative difference) between (or ratio of) the measured 3-IS level and a predetermined control level; and determining, by the processor, at least one of: (i) the existence (or non-existence) of ADHD in the individual as opposed to at least one other condition exclusive of ADHD, wherein the at least one other condition comprises non-ADHD, said identifying based at least in part on the measured 3-IS level and/or the difference between the measured 3-IS level and the predetermined control level (e.g., distinguishing between ADHD and non-ADHD in the individual based at least in part on the measured 3-IS level and/or the difference between the measured 3-IS level and the predetermined control level); and (ii) a likelihood the individual has (or does not have) ADHD as opposed to at least one other condition exclusive of ADHD, wherein the at least one other condition comprises non-ADHD, said identifying based at least in part on the measured 3-IS level and/or the difference between the measured 3-IS level and the predetermined control level.

In some embodiments, the individual is independently suspected of having (e.g., by a medical practitioner) or is independently observed to have (e.g., by a medical practitioner) atypical development, said independent suspicion or observation having been made prior to the identifying step.

In some embodiments, the methods comprise identifying, by the processor of the computing device, the existence of ADHD in the individual as opposed to non-ADHD. In some embodiments, the methods comprise identifying, by the processor of the computing device, a risk score quantifying the likelihood the individual has ADHD as opposed to at least one other condition, wherein the at least one other condition comprises non-ADHD. In some embodiments, the methods comprise identifying, by the processor of the computing device, a risk score quantifying the likelihood the individual has ADHD as opposed to non-ADHD.

In some embodiments, the sample is a blood sample. In some embodiments, the sample comprises plasma. In some embodiments, the sample comprises white blood cells.

In some embodiments, the individual has been identified by a medical practitioner as displaying atypical behavior prior to the identifying step.

In some embodiments, the individual is five years old or less (e.g., three years old or less, 24 months old or less, or 20 months old or less). In some embodiments, the individual is male.

In some embodiments, the invention provides systems for distinguishing between or among at least two conditions for diagnosis and/or risk assessment of an individual suspected of having or observed as having atypical development, wherein the at least two conditions comprise attention deficit hyperactivity disorder (ADHD) and non-attention deficit hyperactivity disorder (non-ADHD), the system comprising:

a diagnostics kit comprising testing instruments for measuring a level of 3-Indoxyl Sulfate (3-IS) in a biological sample obtained from the individual; and a non-transitory computer-readable medium having instructions stored thereon, wherein the instructions, when executed by a processor, cause the processor to:

optionally, identify a difference (e.g., an absolute difference or a relative difference) between (or ratio of) the measured 3-IS level and a predetermined control level; and determine at least one of: (i) the existence (or non-existence) of ADHD in the individual as opposed to at least one other condition exclusive of ADHD, wherein the at least one other condition comprises non-ADHD, based at least in part on the measured 3-IS level and/or the difference between the measured 3-IS level and the predetermined control level (e.g., distinguishing between ADHD and non-ADHD in the individual based at least in part on the measured 3-IS level and/or the difference between the measured 3-IS level and the predetermined control level); and (ii) a likelihood the individual has (or does not have) ADHD as opposed to at least one other condition exclusive of ADHD, wherein the at least one other condition comprises non-ADHD, based at least in part on the measured 3-IS level and/or the difference between the measured 3-IS level and the predetermined control level.

In some embodiments, the diagnostics kit is an in vitro diagnostics kit. In some embodiments, the individual is independently suspected of having (e.g., by a medical practitioner) or is independently observed to have (e.g., by a medical practitioner) atypical development.

In some embodiments, the instructions cause the processor to identify the existence of ADHD in the individual as opposed to non-ADHD (e.g., distinguish between ADHD and non-ADHD). In some embodiments, the instructions cause the processor to identify a risk score quantifying the likelihood the individual has ADHD as opposed to at least one other condition, wherein the at least one other condition comprises non-ADHD. In some embodiments, the instructions cause the processor to identify a risk score quantifying the likelihood the individual has ADHD as opposed to non-ADHD. In some embodiments, the sample is a blood sample. In some embodiments, the sample comprises plasma. In some embodiments, the sample comprises white blood cells.

In some embodiments, the individual has been identified by a medical practitioner as displaying atypical behavior prior to the identifying step. In some embodiments, the individual is five years old or less (e.g., three years old or less, 24 months old or less, or 20 months old or less). In some embodiments, the individual is male.

In some embodiments, the invention provides non-transitory computer-readable media having instructions stored thereon, wherein the instructions, when executed by a processor, cause the processor to:

optionally, identify a difference (e.g., an absolute difference or a relative difference) between (or ratio of) the measured 3-IS level and a predetermined control level; and determine at least one of:

(i) the existence (or non-existence) of ADHD in the individual as opposed to at least one other condition exclusive of ADHD, wherein the at least one other condition comprises non-ADHD, based at least in part on the measured 3-IS level and/or the difference between the measured 3-IS level and the predetermined control level (e.g., distinguishing between ADHD and non-ADHD in the individual based at least in part on the measured 3-IS level and/or the difference between the measured 3-IS level and the predetermined control level); and (ii) a likelihood the individual has (or does not have) ADHD as opposed to at least one other condition exclusive of ADHD, wherein the at least one other condition comprises non-ADHD, based at least in part on the measured 3-IS level and/or the difference between the measured 3-IS level and the predetermined control level.

In some embodiments, the invention provides methods of treating an individual suspected of having or observed as having atypical development, the method comprising the steps of:

obtaining a biological sample from the individual;

measuring a level of 3-Indoxyl Sulfate (3-IS) in the biological sample;

optionally, identifying, by a processor of a computing device, a difference (e.g., an absolute difference or a relative difference) between (or ratio of) the measured 3-IS level and a predetermined control level;

determining the existence of ADHD in the individual as opposed to at least one other condition exclusive of ADHD, wherein the at least one other condition comprises non-ADHD, said identifying based at least in part on the measured 3-IS level and/or the difference between the measured 3-IS level and the predetermined control level (e.g., distinguishing between ADHD and non-ADHD in the individual based at least in part on the measured 3-IS level and/or the difference between the measured 3-IS level and the predetermined control level); and administering therapy to the individual for ADHD.

In some embodiments, the therapy is behavioral therapy. In some embodiments, the therapy comprises administration of a therapeutic substance.

In some embodiments, the sample is a blood sample. In some embodiments, the sample comprises plasma. In some embodiments, the sample comprises white blood cells.

In some embodiments, the individual has been identified by a medical practitioner as displaying atypical behavior prior to the identifying step. In some embodiments, the individual is male.

In some embodiments, the individual is independently suspected of having (e.g., by a medical practitioner) or is independently observed to have (e.g., by a medical practitioner) atypical development, said independent suspicion or observation having been made prior to the identifying step.

In some embodiments, the invention provides methods for determining a condition for diagnosis and/or risk assessment of an individual suspected of having or observed as having atypical development, wherein the at least one condition comprises attention deficit hyperactivity disorder (ADHD), the method comprising the steps of:

measuring a level of 3-Indoxyl Sulfate (3-IS) in a biological sample obtained from the individual;

optionally identifying, by a processor of a computing device, a difference (e.g., an absolute difference or a relative difference) between (or ratio of) the measured 3-IS level and a predetermined control level; and determining, by the processor, at least one of: (i) the existence of ADHD in the individual as opposed to the non-existence of ADHD, wherein the non-existence of ADHD comprises non-ADHD, said identifying based at least in part on the measured 3-IS level and/or the difference between the measured 3-IS level and the predetermined control level (e.g., distinguishing between ADHD and non-ADHD in the individual based at least in part on the measured 3-IS level and/or the difference between the measured 3-IS level and the predetermined control level); and (ii) a likelihood the individual has ADHD as opposed to at least one other condition indicative of atypical development and exclusive of ADHD, wherein the at least one other condition does not comprise ADHD, said identifying based at least in part on the measured 3-IS level and/or the difference between the measured 3-IS level and the predetermined control level.

In some embodiments, the invention provides methods of treating a subject for attention deficit hyperactivity disorder, comprising administering to the subject a composition comprising methylphenidate, dextroamphetamine, dextroamphetamine-amphetamine, lisdexamfetamine, atomoxetine, bupropion, desipramine, clonidine, or guanfacine, wherein a blood sample from the subject has previously been identified as having an elevated level of 3-Indoxyl Sulfate (3-IS) compared to a reference.

In some embodiments, the elevated level of 3-IS is greater than 14 µM. In some embodiments, the elevated level of 3-IS is greater than 457 µg/L. In some embodiments, the level of 3-IS is measured by mass spectrometry.

In some embodiments, the subject is 5 years old or less. In some embodiments, the subject is 3 years old or less. In some embodiments, the subject is 2 years old or less.

In some embodiments, the invention provides methods of identifying a subject for treatment with a therapy for attention deficit hyperactivity disorder, comprising:

obtaining a blood sample from the subject;

measuring 3-Indoxyl sulfate (3-IS) level in the sample by mass spectrometry; and identifying the sample as having a 3-IS level that is higher than a reference level.

In some embodiments, the treatment is a behavioral therapy. In some embodiments, the treatment is selected from the group consisting of methylphenidate, dextroamphetamine, dextroamphetamine-amphetamine, lisdexamfetamine, atomoxetine, bupropion, desipramine, clonidine, guanfacine, and combinations thereof.

In some embodiments, the reference level of 3-IS is 14 µM. In some embodiments, the reference level of 3-IS is 457 µg/L.

In some embodiments, the 3-IS level in the sample is at least 1 fold higher than the reference level. In some embodiments, the 3-IS level in the sample is at least 1.5 higher than the reference level. In some embodiments, the 3-IS level in the sample is at least 2 fold higher than the reference level. In some embodiments, the 3-IS level in the sample is at least 2.5 fold higher than the reference level. In some embodiments, the 3-IS level in the subject is at least 3 fold higher than the reference level. In some embodiments, the 3-IS level in the sample is at least 4 fold higher than the reference level.

BRIEF DESCRIPTION OF THE DRAWING

FIG. 1 shows normalized density levels of 3-Indoxyl sulfate (3-IS) in plasma from a group of subjects previously diagnosed as having ADHD or not having ADHD.

DETAILED DESCRIPTION

Methods and systems are presented herein to distinguish individuals with Attention Deficit Hyperactivity Disorder (ADHD) from those without Attention Deficit Hyperactivity Disorder (non-ADHD) based at least in part on level of 3-Indoxyl sulfate (3-IS) in a biological sample taken from an individual. In certain embodiments, other metabolites, biochemical markers, and/or biophysical markers can also be used when distinguishing ADHD from non-ADHD.

It is found that determining the level of 3-IS in a biological sample (e.g., plasma) is useful in providing an objective method of diagnosing and/or identifying a risk factor for ADHD as distinguished from non-ADHD.

3-Indoxyl Sulfate (3-IS)

3-Indoxyl sulfate, also known as Indoxyl sulfate, is a dietary protein metabolite and a metabolite of the common amino acid tryptophan. 3-IS is a circulating uremic toxin stimulating glomerular sclerosis and interstitial fibrosis. In plasma, 3-IS is a protein-bound uremic solute that induces endothelial dysfunction by inhibiting endothelial proliferation and migration in vitro. Some studies suggest that 3-IS is also involved in oxidative stress. In hemodialyzed patients, serum levels of 3-IS are associated with levels of pentosidine, a marker of carbonyl and oxidative stress. In vitro, Indoxyl sulfate has been shown to increase reactive oxygen species (ROS) production in tubular cells, and increase NAD(P)H oxidase activity in endothelial cells. 3-IS is also associated with a decrease in levels of the active antioxidant glutathione in cells.

Concentrations of 3-IS in the blood of adults has been reported to be on average approximately 2.49 to 14 µM. (See, e.g., Duranton F et al., (2012) J Am Soc Nephrol. July; 23(7):1258-70. Epub 2012 May 24, reporting 2.49+/−1.36 µM in a normal population of 18 years and older males and females; and Geigy Scientific Tables, 8th Rev edition, pp. 165-177. Edited by C. Lentner, West Cadwell, N.J.: Medical education Div., Ciba-Geigy Corp., Basel, Switzerland, reporting 14.0+/−4.2 µM in a normal population of 18 years and older males; the disclosure of each of which pertaining to Indoxyl sulfate incorporated herein by reference).

In a pediatric population, blood levels of normal subjects (i.e., without ADHD) have been reported to be approximately 457.5+/−228.5 µg/L (see Umino et al., *Pediatrics International* (2010) 52:257-261, incorporated herein by reference in its entirety.

In some embodiments a reference blood concentration of 3-IS in normal subjects (without ADHD) is from about 2.5 µM to about 14.0 µM. In some embodiments a reference blood concentration of 3-IS in normal subject is about 2.5 µM. In some embodiments, a reference blood concentration of 3-IS in normal subjects is about 14.0 µM. In some embodiments, a reference blood concentration of 3-IS in normal subjects (i.e., without ADHD) is from about 229 µg/L to about 686 µg/L. In some embodiments, a reference blood concentration of 3-IS in normal subjects (i.e., without ADHD) is about 457.5 µg/L.

Treatment of Attention Deficit Hyperactivity Disorder (ADHD)

Standard treatments for ADHD in children include medications, education, training and counseling. Currently, stimulant drugs (psychostimulants) are commonly prescribed medications for ADHD. Stimulants appear to boost and balance brain levels of levels of neurotransmitters and help improve the signs and symptoms of inattention and hyperactivity. Examples include methylphenidate (CONCERTA, METADATE, RITALIN), dextroamphetamine (DEXEDRINE), dextroamphetamine-amphetamine (ADDERALL XR) and lisdexamfetamine (VYVANSE). Stimulant drugs are available in short-acting and long-acting forms.

Other medications used to treat ADHD include atomoxetine (STRATERRA) and antidepressants such as bupropion (WELLBUTRIN, others) and desipramine (NORPRAIVIIN). Clonidine (CATAPRES) and guanfacine (INTUNIV, TENEX) have also been shown to be effective. Atomoxetine and antidepressants may take several weeks before they take full effect.

Children with ADHD often benefit from behavior therapy and counseling, which may be provided by a psychiatrist, psychologist, social worker or other mental health care professional. Some children with ADHD may also have other conditions such as anxiety disorder or depression. In these cases, counseling may help both ADHD and the coexisting problem. Examples of therapy include: behavioral therapy, psychotherapy, social skills training, and family therapy.

In one aspect, the invention is directed to a method for distinguishing between or among at least two conditions for diagnosis and/or risk assessment of an individual suspected of having or observed as having atypical development, wherein the at least two conditions comprise attention deficit hyperactivity disorder (ADHD) and non-attention deficit hyperactivity disorder (non-ADHD), the method comprising the steps of: measuring a level of 3-Indoxyl Sulfate (3-IS) in a biological sample obtained from the individual; optionally, identifying, by a processor of a computing device, a difference (e.g., an absolute difference or a relative difference) between (or ratio of) the measured 3-IS level and a predetermined control level; and determining, by the processor, at least one of: (i) the existence (or non-existence) of ADHD in the individual as opposed to at least one other condition exclusive of ADHD, said identifying based at least in part on the measured 3-IS level and/or the difference between the measured 3-IS level and the predetermined control level (e.g., distinguishing between ADHD and non-ADHD in the individual based at least in part on the measured 3-IS level and/or the difference between the measured 3-IS level and the predetermined control level); and (ii) a likelihood the individual has (or does not have) ADHD as opposed to at least one other condition, said identifying based at least in part on the measured 3-IS level and/or the difference between the measured 3-IS level and the predetermined control level.

In some embodiments, the individual is independently suspected of having (e.g., by a medical practitioner) or is independently observed to have (e.g., by a medical practitioner) atypical development, said independent suspicion or observation having been made prior to the identifying step. In some embodiments, the method comprises identifying, by the processor of the computing device, the existence of ADHD in the individual as opposed to non-ADHD.

In some embodiments, the method comprises identifying, by the processor of the computing device, a risk score quantifying the likelihood the individual has ADHD as opposed to at least one other condition. In some embodiments, the method comprises identifying, by the processor of the computing device, a risk score quantifying the likelihood the individual has ADHD as opposed to non-ADHD.

In some embodiments, the sample is a blood sample. In some embodiments, the sample comprises plasma. In some embodiments, the sample comprises white blood cells. In some embodiments, the sample comprises cerebrospinal fluid. In some embodiments, the sample comprises urine.

In some embodiments, the individual has been identified by a medical practitioner as displaying atypical behavior prior to the identifying step. In some embodiments, the individual is five years old or less (e.g., three years old or less, 24 months old or less, or 20 months old or less).

In some embodiments, the individual is male.

In another aspect, the invention is directed to a system for distinguishing between or among at least two conditions for diagnosis and/or risk assessment of an individual suspected of having or observed as having atypical development, wherein the at least two conditions comprise attention deficit hyperactivity disorder (ADHD) and non-attention deficit hyperactivity disorder (non-ADHD), the system comprising: a diagnostics kit comprising testing instruments for measuring a level of 3-Indoxyl Sulfate (3-IS) in a biological sample obtained from the individual; and a non-transitory computer-readable medium having instructions stored thereon, wherein the instructions, when executed by a processor, cause the processor to:

optionally, identify a difference (e.g., an absolute difference or a relative difference) between (or ratio of) the measured 3-IS level and a predetermined control level; and determine at least one of: (i) the existence (or non-existence) of ADHD in the individual as opposed to at least one other condition, wherein the at least one other condition comprises non-ADHD, based at least in part on the measured 3-IS level and/or the difference between the measured 3-IS level and the predetermined control level (e.g., distinguishing between ADHD and non-ADHD in the individual based at least in part on the measured 3-IS level and/or the difference between the measured 3-IS level and the predetermined control level); and (ii) a likelihood the individual has (or does not have) ADHD as opposed to at least one other condition, based at least in part on the measured 3-IS level and/or the difference between the measured 3-IS level and the predetermined control level.

In some embodiments, the diagnostics kit is an in vitro diagnostics kit. In some embodiments, the individual is independently suspected of having (e.g., by a medical practitioner) or is independently observed to have (e.g., by a medical practitioner) atypical development.

In some embodiments, the instructions cause the processor to identify the existence of ADHD in the individual as opposed to non-ADHD (e.g., distinguish between ADHD and non-ADHD). In some embodiments, the instructions cause the processor to identify a risk score quantifying the likelihood the individual has ADHD as opposed to at least one other condition, wherein the at least one other condition comprises non-ADHD. In some embodiments, the instructions cause the processor to identify a risk score quantifying the likelihood the individual has ADHD as opposed to non-ADHD.

In some embodiments, the sample is a blood sample. In some embodiments, the sample comprises plasma. In some embodiments, the sample comprises white blood cells. In some embodiments, the sample comprises cerebrospinal fluid. In some embodiments, the sample comprises urine.

In some embodiments, the individual has been identified by a medical practitioner as displaying atypical behavior prior to the identifying step. In some embodiments, the individual is five years old or less (e.g., three years old or less, 24 months old or less, or 20 months old or less).

In some embodiments, the individual is male.

In another aspect, the invention is directed to a non-transitory computer-readable medium having instructions stored thereon, wherein the instructions, when executed by a processor, cause the processor to: optionally, identify a difference (e.g., an absolute difference or a relative difference) between (or ratio of) the measured 3-IS level and a predetermined control level; and determine at least one of: (i) the existence (or non-existence) of ADHD in the individual as opposed to at least one other condition exclusive of ADHD, wherein the at least one other condition comprises non-ADHD, based at least in part on the measured 3-IS level and/or the difference between the measured 3-IS level and the predetermined control level (e.g., distinguishing between ADHD and non-ADHD in the individual based at least in part on the measured 3-IS level and/or the difference between the measured 3-IS level and the predetermined control level); and (ii) a likelihood the individual has (or does not have) ADHD as opposed to at least one other condition, wherein the at least one other condition comprises non-ADHD, based at least in part on the measured 3-IS level and/or the difference between the measured 3-IS level and the predetermined control level.

In another aspect, the invention is directed to a method of treating an individual suspected of having or observed as having atypical development, the method comprising the steps of: obtaining a biological sample from the individual; measuring a level of 3-Indoxyl Sulfate (3-IS) in the biological sample; optionally, identifying, by a processor of a computing device, a difference (e.g., an absolute difference or a relative difference) between (or ratio of) the measured 3-IS level and a predetermined control level; and determining the existence of ADHD in the individual as opposed to at least one other condition, wherein the at least one other condition comprises non-ADHD, said identifying based at least in part on the measured 3-IS level and/or the difference between the measured 3-IS level and the predetermined control level (e.g., distinguishing between ADHD and non-ADHD in the individual based at least in part on the measured 3-IS level and/or the difference between the measured 3-IS level and the predetermined control level); and administering therapy to the individual for ADHD.

In some embodiments, the therapy is behavioral therapy. In some embodiments, the therapy comprises administration of a therapeutic substance.

In some embodiments, the sample is a blood sample. In some embodiments, the sample comprises plasma. In some embodiments, the sample comprises white blood cells. In some embodiments, the sample comprises cerebrospinal fluid.

In some embodiments, the individual has been identified by a medical practitioner as displaying atypical behavior prior to the identifying step. In some embodiments, the individual is five years old or less (e.g., three years old or less, 24 months old or less, or 20 months old or less).

In some embodiments, the individual is male.

In some embodiments, the individual is independently suspected of having (e.g., by a medical practitioner) or is independently observed to have (e.g., by a medical practitioner) atypical development, said independent suspicion or observation having been made prior to the identifying step.

In another aspect, the invention is directed to a method of determining a condition for diagnosis and/or risk assessment of an individual suspected of having or observed as having atypical development, wherein the at least one condition comprises attention deficit hyperactivity disorder (ADHD), the method comprising the steps of: measuring a level of 3-Indoxyl Sulfate (3-IS) in a biological sample obtained from the individual; optionally identifying, by a processor of a computing device, a difference (e.g., an absolute difference or a relative difference) between (or ratio of) the measured 3-IS level and a predetermined control level; and determining, by the processor, at least one of: (i) the existence of ADHD in the individual as opposed to the nonexistence of ADHD, wherein the non-existence of ADHD comprises non-ADHD, said identifying based at least in part on the measured 3-IS level and/or the difference between the measured 3-IS level and the predetermined control level (e.g., distinguishing between ADHD and non-ADHD in the individual based at least in part on the measured 3-IS level and/or the difference between the measured 3-IS level and the predetermined control level); and (ii) a likelihood the individual has ADHD as opposed to at least one other condition indicative of atypical development, wherein the at least one other condition comprises non-ADHD, said identifying based at least in part on the measured 3-IS level and/or the difference between the measured 3-IS level and the predetermined control level.

Methods and systems are presented herein to distinguish a child with attention deficit hyperactivity disorder (ADHD) from those with non-attention deficit hyperactivity disorder (non-ADHD) based at least in part on the measured 3-IS level in a biological sample of the child.

EXAMPLES

This study used blood samples from subjects in the SynapDx Autism Spectrum Disorder Gene Expression Analysis (STORY) study. The STORY study was performed in accordance with current ICH guidelines on Good Clinical Practice (GCP), and applicable regulatory requirements. GCP is an international ethical and scientific quality standard for designing, conducting, recording, and reporting studies that involve the participation of human subjects. Compliance with this standard provides public assurance that the rights, safety, and wellbeing of study subjects are protected, consistent with the principles that have originated in the Declaration of Helsinki and that the clinical study data are credible.

Results are based on 800 samples from the STORY study. The sample set included 30 (24 males/6 females) known samples from subjects diagnosed with ADHD out of a total number of 800 samples. Machine learning results, using a subset of metabolites, yielded AUCs of 0.60 (matched by age, ethnicity and gender), and 0.73 (all samples). ADHD diagnosis can be based on DSM diagnostic criteria. Blood was collected in EDTA tubes, and plasma was prepared by centrifuging the tubes. The plasma was then frozen and shipped to a laboratory for analysis. At the laboratory, MeOH extraction of the samples was conducted, and the extracts were analyzed by an LC/MS method. An example of this method can be found in Evans AM et al, *Anal. Chem.* (2009) 81(16):6656-6667, the entirety of which is herein incorporated by reference.

FIG. 1 shows the distributions of normalized (to all tested samples) amounts of 3-Indoxyl Sulfate (3-IS) in the plasma of children with ADHD or of children with non-ADHD. The plot shows log transformed values. Twenty-three percent of subjects with known ADHD were also co-diagnosed with Autism Spectrum Disorder (ASD). Examples of methods and systems for determining risk of ASD can be found in U.S. application No. filed Sep. 22, 2014 and Ser. No. 14/633,558, filed Feb. 27, 2015, the entireties of each of which are herein incorporated by reference.

In view of the structure, functions and apparatus of the systems and methods described here, in some implementations, a systems, methods, and apparatus for distinguishing between or among at least two conditions (e.g., ADHD and non-ADHD) for diagnosis and/or risk assessment of an individual suspected of having or observed as having atypical development are provided. Having described certain implementations of methods, systems, and apparatus herein, it will now become apparent to one of skill in the art that other implementations incorporating the concepts of the disclosure may be used. Therefore, the disclosure should not be limited to certain implementations, but rather should be limited only by the spirit and scope of the following claims.

What is claimed is:

1. A method of measuring an increase in 3-Indoxyl Sulfate (3-IS) in a human subject suspected of having or observed to have atypical development for determination of the presence of attention deficit hyperactivity disorder (ADHD), the method comprising:
   obtaining a blood sample from the subject;
   measuring a 3-IS level in the sample by mass spectrometry;
   and determining that the subject has ADHD when the measured 3-IS level in the blood sample is higher than a reference level, wherein the reference level is a level of 3-IS derived from subjects who do not have ADHD.

2. The method of claim 1, wherein the reference level of 3-IS is 14 µM.

3. The method of claim 1, wherein the reference level of 3-IS is 457 µg/L.

4. The method of claim 1, wherein the 3-IS level in the sample is at least 1 fold higher than the reference level.

5. The method of claim 1, wherein the 3-IS level in the sample is at least 1.5 higher than the reference level.

6. The method of claim 1, wherein the 3-IS level in the sample is at least 2 fold higher than the reference level.

7. The method of claim 1, wherein the 3-IS level in the sample is at least 2.5 fold higher than the reference level.

8. The method of claim 1, wherein the 3-IS level in the subject is at least 3 fold higher than the reference level.

9. The method of claim 1, wherein the 3-IS level in the sample is at least 4 fold higher than the reference level.

10. The method of claim 1, wherein the subject has been identified by a medical practitioner as displaying atypical behavior prior to the measuring step.

11. The method of claim 1, wherein the subject is 5 years old or less.

12. The method of claim 1, wherein the subject is 3 years old or less.

* * * * *